United States Patent [19]

Sloan et al.

[11] Patent Number: 5,610,160
[45] Date of Patent: Mar. 11, 1997

[54] TOPICAL 5-FLUOROURACIL PRODRUG COMPOSITION AND METHOD

[76] Inventors: Kenneth B. Sloan, 3551 NW. 23 Pl., Gainesville, Fla. 32605; Howard D. Beall, 4507 SW. 83rd Dr., Gainesville, Fla. 32608

[21] Appl. No.: 347,108

[22] Filed: Nov. 22, 1994

Related U.S. Application Data

[63] Continuation of Ser. No. 680,945, Apr. 5, 1991, abandoned.

[51] Int. Cl.$^6$ .................................................. A61K 31/505
[52] U.S. Cl. ............................................................ 514/274
[58] Field of Search ............................................. 514/274

[56] References Cited

U.S. PATENT DOCUMENTS

| | | |
|---|---|---|
| 4,411,893 | 10/1983 | Johnson et al. ............... 514/274 X |
| 4,845,081 | 7/1989 | Sloan ................................ 514/232.2 |
| 4,853,388 | 8/1989 | Pearlman ............................ 514/274 |

OTHER PUBLICATIONS

Buur et al, *J. Pharm. Sci.*, vol. 75, No. 5, "Prodrugs of 5–Fluorouracil. V. 1–Alkoxycarbonyl Derivatives as Potential Prodrug Forms for Improved Rectal or Oral Delivery of 5–Fluorouracil," pp. 522–527 (1986).

Buur et al, *Acta. Pharm. Suec.*, vol. 23, "Prodrugs of 5–fluorouracil. VII. Hydrolysis kinetics and physico–chemical properties of N–ethoxy– and N–phenoxycarbonyl–oxymethyl derivatives of 5–fluorouracil," pp. 205–216 (1986).

Burr et al, *Int. J. Pharm.*, vol. 36, "Prodrugs of 5–fluorouracil. VIII. Improved rectal and oral delivery of 5–fluorouracil via various prodrugs. Structure–rectal absorption relationships," pp. 41–49 (1987).

Kametani et al, *J. Med. Chem.*, vol. 23, "Studies on the Synthesis of Chemotherapeutics. 10. Synthesis and Anti–tumor Activity of N–Acyl– and N–(Alkoxycarbonyl)–5–fluorouracil Derivatives," pp. 1324–1329 (1980).

Kametani et al, *J. Med. Chem.*, vol. 25, "Studies on the Synthesis of Chemotherapeutics. 12. Synthesis and Anti–tumor Activity of N–Phthalidyl–5–fluorouracil Derivatives," pp. 1219–1222 (1982).

Buur et al, *Int. J. Pharm.*, vol. 21, "Prodrugs of 5–fluorouracil. I. Hydrolysis kinetics and physico–chemical properties of various N–acyl derivatives of 5–fluorouracil," pp. 349–364 (1984).

*Primary Examiner*—Raymond Henley, III
*Attorney, Agent, or Firm*—Dennis P. Clarke; Kerkam, Stowell, Kondracki & Clarke, PC

[57] ABSTRACT

A pharmaceutical composition in unit dosage form adapted for topical administration to a human or non-human animal in need thereof comprising a pharmacologically effective amount of a prodrug of 5-fluorouracil having the formula:

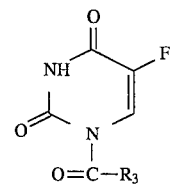

wherein $R_3$ is bonded to C=O by a carbon-to-carbon bond and is a group such that the prodrug (1) has an enhanced delivery across topical membranes and (2) hydrolyzes after delivery to 5-fluorouracil.

10 Claims, No Drawings

TOPICAL 5-FLUOROURACIL PRODRUG COMPOSITION AND METHOD

This application is a continuation of application Ser. No. 07/680,945, filed Apr. 5, 1991, now abandoned.

BACKGROUND OF THE INVENTION

1. Field of the Invention

The present invention relates to certain 5-fluorouracil prodrug compositions and methods for their topical administration.

2. Description of the Prior Art

Considerable research has been conducted in an attempt to solve the problem of enhancing the delivery of topically applied drugs across the topical skin membrane.

Many drugs have been found to be useful for the treatment of various skin disease states such as psoriasis and atopic dermatitis when they are given orally, but are not effective when applied topically. However, the use of a drug in a topical manner to treat a topical disease state is desirable in that only a locally effective concentration of the drug needs to be attained in the skin. On the other hand, an oral dose develops a systemic (whole body) concentration of the drug.

Although 5-fluorouracil (5-FU) is the only widely accepted topical treatment for skin malignancies and is successful in treating superficial lesions such as actinic keratoses [Dillaha et al, *Arch. Dermatol*, Vol. 92, page 410 (1965)] and basal cell carcinomas [Sloan et al, *Int. J. Pharm.*, Vol. 44, page 87 (1988)], it is ineffective in treating deeper lesions or actinic keratoses of the extremities. Therefore, a more effective and less irritating therapy is generally conceded as being desirable.

There are two general approaches to enhancing the dermal delivery of any drug. The first is by a formulation approach and the second is by a prodrug approach [Waranis et al, *J. Pharm. Sci.*, Vol. 76, page 587 (1987)].

Prodrugs comprise derivatized or other chemical and/or physically modified forms of the drug species and are designed to more readily penetrate topical barriers. Upon transport across the topical membrane, they are converted in situ to the active form, whereupon they perform their intended biological function in the target organ. These prodrugs are also designed to resist metabolic conversions and other forms of degradation until they have crossed the barrier.

5-FU is conventionally employed in a formulation containing propylene glycol (a solubilizer) and a penetration enhancer. See U.S. Pat. Nos. 3,991,203; 4,411,893; 4,415,563; 4,714,703 and 4,853,388; and Japanese Patent No. 83-79915 [abstracted in *Chem. Abs.*, Vol. 99:58911h (1983)]. Propylene glycol is very irritating to the skin over extended courses of treatment which can last for several weeks.

Polar, high-melting, heterocyclic drugs such as 5-FU which are relatively insoluble in lipids and in water have presented a challenge to pharmaceutical chemists for some time in their efforts to improve the topical delivery of such agents so that they can be used effectively in clinical situations. One approach to meeting this challenge has been to use N-acyloxyalkyl prodrug derivatives which are lower-melting and more lipophilic than the parent drugs. Recently, a number of examples of the application of this approach to modifying heterocyclic drugs have been described [Bodor et al, U.S. Pat. No. 4,061,753; CA 87:152278 (1977) and Sloan et al, *Int. J. Pharm.*, Vol. 12, pages 299–313 (1982); Stella et al, U.S. Pat. No. 4,163,058; CA 91:193312 (1979); Ozaki et al, U.S. Pat. No. 4,267,326; Mollgaard et al, *Int. J. Pharm.*, Vol. 12, pages 153–162 (1982); and Sloan et al, *J. Pharm. Sci.*, Vol. 72, pages 372–378 (1983)].

Although no examples of prodrugs have been reported where both water and lipid solubility have been optimized in order to obtain enhanced delivery of drugs across topical membranes, there are a number of prodrugs which incorporate an amino group into the derivative and exhibit enhanced lipid solubility and dermal delivery [Sloan, U.S. Pat. No. 4,206,220; CA 93:8017 (1980); Sloan and Little, CA 96:104087 (1982); Sloan, CA 97:144855 (1982); and Bodor et al, *Int. J. Pharm.*, Vol. 10, pages 307–321 (1982)].

Although the topical membrane or skin is a "biological membrane," it differs substantially from other membranes in that the barrier to absorption of drugs is the stratum corneum which comprises a dead, dry (5–10% $H_2O$), compact keratin-containing material. All other biological membranes comprise live, essentially aqueous (75–80% $H_2O$) material. Obviously, therefore, the considerations bearing on the transport or delivery of drug species across other biological membranes are altogether different from those bearing on the delivery of drugs across the topical skin membrane.

A high degree of lipophilicity is necessary in any prodrug designed to effectively cross the skin membrane. However, the prodrug must substantially immediately convert to the parent active drug species after transport across the stratum corneum.

It has been suggested heretofore to employ certain N-Mannich type bases as prodrugs for oral or parenteral administration. See, for example, Pitman. *Med. Res. Rev.*, Vol. 1, No. 2, pages 189–214 (1981); Johansen et al, *Arch. Pharm. Chem. Sci.*, Ed. 8, pages 141–151, 207–214 (1980); Johansen et al, *Arch. Pharm. Chem. Sci.*, Ed. 10, pages 111–121 (1982); Bundgaard et al, *Int. J. Pharm.*, Vol. 7, pages 119–127, 129–136 (1980); Bundgaard et al, *J. Pharm. Sci.*, Vol. 69, No. 1, pages 44–47 (1980); Bundgaard et al, *Acta. Pharm. Suec.*, Vol. 18, pages 129–134 (1981); Bundgaard et al, *Int. J. Pharm.*, Vol. 8, pages 183–192 (1981); and Bundgaard et al, *Int. J. Pharm.*, Vol. 9, pages 7–16 (1981). There is no suggestion in the prior art, however, as to the utilization of such N-Mannich bases as topical prodrugs.

There is disclosed in U.S. Pat. No. 4,412,994 the use of Mannich base hydroxamic acid prodrugs for topical administration to warm-blooded animals. The parent drugs from which the prodrugs are derived, however, are limited to "acyl residues of non-steroidal anti-inflammatory agents containing a carboxylic acid function."

The use of Mannich bases or aminomethyl derivatives for topical delivery involves the intact prodrug partitioning from a non-protic solvent (in which it is stable) into the skin (in which it is not stable because of the presence of water) where it reverts to the parent compound. On the other hand, the use of Mannich bases or aminomethyl derivatives for oral or parenteral use take advantage of increased water solubility and increased dissolution properties of the derivatives to enhance the bio-availability of the parent drug, but it is the parent drug and not the prodrug that is actually involved in the partitioning from the aqueous environment (in which the prodrug is not stable) into the membranes and from there ultimately the systemic circulation. Thus, the topical delivery depends on the superior partitioning properties of the intact prodrug while the oral or parenteral delivery still depends on partitioning properties of the parent drug and gains its only advantage from the more immediate and higher solution concentrations of the parent drug that develop from the use of the prodrugs.

Sloan (U.S. Pat. No. 4,845,081) describes certain aminomethyl derivatives of 5-FU as well as other biologically active organic compounds which function successfully as topically applied prodrugs having an enhanced delivery or transport across the topical membrane.

It is an object of the present invention to provide novel 5-fluorouracil prodrug compositions and methods for their topical administration.

SUMMARY OF THE INVENTION

The above and other objects are realized by the present invention which provides a pharmaceutical composition in unit dosage form adapted for topical administration to a human or non-human animal in need thereof comprising a pharmacologically effective amount of a prodrug of 5-fluorouracil having the formula:

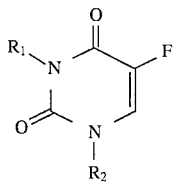

wherein: $R_1$ and $R_2$ may be the same or different and are selected from the group consisting of H, $R_3CO-$ and $R_4-O-CO$ with the proviso that both $R_1$ and $R_2$ may not be H;

or a non-toxic pharmaceutically acceptable salt, adduct, oxide or other derivative thereof; and a pharmaceutically acceptable, topically administrable carrier therefor; said $R_3$ and $R_4$ comprising groups such that the prodrug (1) has an enhanced delivery across topical membranes of the animal upon topical application of the composition as compared with 5-fluorouracil and (2) hydrolyzes after delivery across the topical membrane to yield a pharmacologically effective amount of 5-fluorouracil.

Another embodiment of the invention comprises a method of administering 5-fluorouracil to a human or non-human animal in need thereof comprising topically applying to the animal a pharmacologically effective amount of the above-described composition.

DETAILED DESCRIPTION OF THE INVENTION

Several of the above-described compounds have been characterized in the prior art as prodrugs for the improved rectal or oral delivery of 5-FU. See Kametani et al, *J. Med. Chem.*, Vol. 23, pages 1324–1329 (1980) and *J. Med. Chem.*, Vol. 25, pages 1219–1222 (1982); *J. Pharm. Sci.*, Vol. 75, No. 5, pages 522–527 (1986); and *Acta. Pharm. Suec.*, Vol. 23, pages 205–216 (1986).

The present invention is predicated on the discovery that these and related compounds are also effective prodrugs for the enhanced delivery or transport of 5-FU across topical membranes.

In the structural formula set forth above, $R_3$ and $R_4$ may be the same or different and are selected from the group consisting of (a) cycloalkyl groups having one to ten carbon atoms, (b) straight or branched chain alkyl groups of one to ten carbon atoms, (c) straight or branched chain alkenyl or alkynyl groups of two to ten carbon atoms, wherein the chains of (a), (b) or (c) thereof (1) may be interrupted by one or more N, S or O atoms, or (2) may be substituted at any point on the chain by one or more members selected from the group consisting of $COR_5$, $COOR_5$, $CON(R_5)_2$ and mono- and bi-cyclic saturated or unsaturated heterocyclic rings, each ring consisting of three to seven members selected from the group consisting of C, N, O and S, hydrocarbyl aryl groups, aryl groups substituted by at least one member selected from the group consisting of $COR_5$, $COOR_5$, $CON(R_5)_2$, $OR_5$, halogen, $SR_5$, $N(R_5)_2$, $NO_2$ and $R_5$, and mono- and bi-cyclic saturated or unsaturated heterocyclic rings, each ring consisting of three to seven members selected from the group consisting of C, N, O and S.

Most preferably, $R_3$ is $CH_3$ or $C_2H_5$, and $R_4$ is $C_2H_5$.

$R_5$ is selected from the group consisting of cycloalkyl or straight or branched chain alkyl groups of one to ten carbon atoms, and alkenyl or alkynyl groups of two to ten carbon atoms.

Either of $R_1$ or $R_2$ may be H; however, as will be apparent, both may not be H since the resulting compound would be 5-FU.

Preferred embodiments of the invention are those compositions and methods wherein the structural formula of the prodrug is:

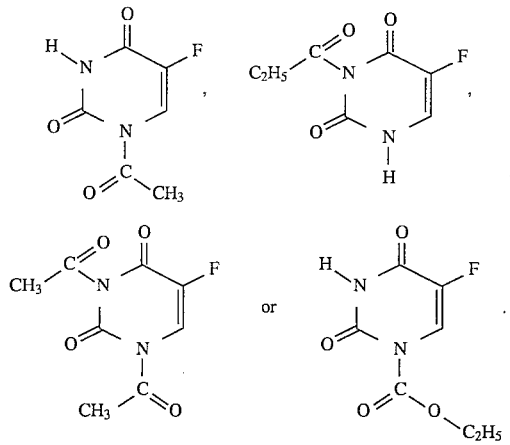

The compositions of the invention for both veterinary and for human use of the present invention comprise the prodrug together with one or more acceptable carriers therefor and optionally other therapeutic ingredients. The carrier(s) must be "acceptable" in the sense of being compatible with the other ingredients of the formulations, not deleterious to the recipient thereof and suitable for topical application. The formulations may conveniently be presented in unit dosage form and may be prepared by any of the methods well known in the art of pharmacy. All methods include the step of bringing into association the prodrug with the carrier which constitutes one or more accessory ingredients. In general, the formulations are prepared by uniformly and intimately bringing into association the prodrug with the carrier(s) and then, if necessary, dividing the product into unit dosages thereof.

It should be understood that excluded from the scope of the present invention are non-sterile mixtures which are merely solutions or suspensions of the known prodrugs in solvents and liquids known in the literature for use in their synthesis and/or isolation by the methods described therein. Included within the scope of the present invention are such solutions and suspensions of the known substances which are pharmaceutically acceptable to the intended recipient thereof and which contain in addition at least one other pharmaceutically acceptable substance.

Suitable non-toxic pharmaceutically acceptable carriers for use with the prodrugs will be apparent to those skilled in the art. See, for example, *Remington's Pharmaceutical Sciences,* 4th edition (1970). Obviously, the choice of suitable carriers will depend upon the exact nature of the particular dosage form selected, as well as upon the identity of the prodrug species.

Generally, however, the prodrugs of the present invention for use in topical applications should be restricted to use in non-protic, anhydrous vehicles (e.g., plastibase, petrolatum, isopropyl, myristate, etc.) at concentrations of from about 0.1 to about 20% by weight. The stability of the prodrug in a particular vehicle will depend upon the vehicle employed.

The therapeutic dosage ranges for administration of the prodrugs will generally be the same as, or less than, those characteristically used in this art for administration of the active drug species. Obviously, such therapeutic dosage ranges will vary with the size of the patient, the condition for which the prodrug is administered, the particular dosage form employed and the like. The quantity of given dosage form required to deliver the desired dose of the active drug 5-FU will, of course, depend upon the concentration of the prodrug in any given pharmaceutical composition dosage thereof.

The invention is illustrated by the following non-limiting examples.

EXAMPLE 1

Syntheses

The 1-alkylcarbonyl derivatives (1–6) in Tables 1 and 2 were synthesized from the reaction of the potassium salt of 5-FU with the corresponding acyl chlorides in acetone or acetonitrile at ice-bath temperature. The 1-alkyloxycarbonyl derivatives (7–12) in Tables 3–5 were synthesized from the reaction of the potassium salt of 5-FU with the corresponding alkyl chloroformates in acetone at room temperature for one hour. The 3-alkylcarbonyl derivatives (13–16) in Tables 6–8 were synthesized from the reaction of the corresponding 1,3-bisalkylcarbonyl derivatives with one equivalent of t-butylamine in ether at room temperature until the reaction was complete by TLC. The 1,3-bisalkylcarbonyl derivatives (17–20) in Tables 9 and 10 were synthesized from the reaction of 5-FU with three equivalents of the corresponding acyl chlorides in the presence of three equivalents of triethylamine at room temperature for three hours.

EXAMPLE 2

Diffusion Cell Experiments

The diffusion cell experiments were conducted as described by Sloan et al in *J. Invest. Dermatol.,* Vol. 87, page 244 (1986), and Sherertz et al in *J. Invest. Dermatol.,* Vol. 89, page 147 (1987). The results from these experiments are recorded in the tables as $J_i$ (flux of 5-FU through the skin indicating the relative extent of transdermal delivery), $C_s$ (a measure of the amount of 5-FU in the skin after the applied formulation of prodrug was removed indicating the relative extent of dermal delivery) and $J_j$ (flux of a standard drug/formulation through the skin after the application of the prodrug/formulation indicating the relative amount of damage caused by the prodrug/formulation).

EXAMPLE 3

Physicochemical Properties

The results from the determination of the physicochemical properties are recorded in the tables as $C_{IPM}$ (the saturated solubility of the prodrug in the isopropyl myristate (IPM) vehicle/formulation in which the prodrug was applied to the mouse skins), K (the partition coefficients of the prodrug between IPM and a pH 4.0 acetate buffer) and $C_w$ (the solubility of the prodrug in pH 4.0 acetate buffer calculated from the partition coefficient and the IPM solubility). Because some of the prodrugs were so unstable in the presence of protic solvents, the partition coefficients were determined by vigorously shaking 0.5 to 1.0 ml of the IPM solutions from the IPM solubility determinations with 0.5–1.0 ml of the buffer for ten seconds, allowing the layers to separate for sixty seconds, and analyzing the IPM solutions for intact prodrug immediately.

TABLE 1

PHYSICOCHEMICAL PROPERTIES OF
1-ALKYLCARBONYL DERIVATIVES OF 5-FU

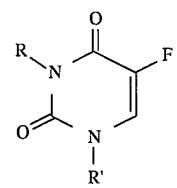

| Compound | MP °C. | K[a] | $C_w$[b] |
|---|---|---|---|
| 1. R = H, R' = (C=O)CH$_3$ | 126–127 | 0.185 | 20.7 |
| 2. R = H, R' = (C=O)C$_2$H$_5$ | 127–128 | 0.764 | 8.86 |
| 3. R = H, R' = (C=O)C$_3$H$_7$ | 142–143 | 2.69 | 1.30 |
| 4. R = H, R' = (C=O)C$_4$H$_9$ | 117–118 | 11.3 | 0.745 |
| 5. R = H, R' = (C=O)C$_5$H$_{11}$ | 98–99 | 42.9 | 0.662 |
| 6. R = H, R' = (C=O)C$_7$H$_{15}$ | 81–82 | — | — |

[a]Partition coefficient between IPM and pH 4.0 acetate buffer at 23 ± 1° C.
[b]Solubility in mg/ml of pH 4.0 acetate buffer at 23 ± 1° C. calculated from partition coefficient between IPM and pH 4.0 acetate buffer and the solubility of derivative in IPM.

TABLE 2

RATES OF DELIVERY OF 5-FU THROUGH
HAIRLESS MOUSE SKIN BY
1-ALKYLCARBONYL DERIVATIVES OF 5-FU

| Compound | $C_{IPM}$[a] | $J_i$[b] | $C_s$[c] | $J_j$[d] |
|---|---|---|---|---|
| 5-FU | 0.0064 | 0.0311 | 0.48 | 0.215 |
| 1 | 3.80 (2.87) | 1.213 | 8.85 | 0.296 |
| 2 | 6.77 (4.73) | 0.560 | 8.96 | 0.219 |
| 3 | 3.48 (2.26) | 0.168 | 1.07 | 0.185 |
| 4 | 8.39 (5.10) | 0.133 | 2.08 | 0.144 |
| 5 | 25.7 (14.6) | 0.146 | 1.42 | 0.084 |
| 6 | 28.4 (14.4) | 0.078 | 1.58 | 0.129 |

[a]Solubility in mg/ml of IPM at 23 ± 1° C. (equivalent mg of 5-FU/ml).
[b]Flux in mg/cm$^2$ hour of 5-FU from suspensions of prodrugs in IPM.
[c]Amount of 5-FU in mg leached from hairless mouse skin in 24 hours subsequent to application of prodrug in vehicle for 48 hours.
[d]Flux in mg/cm$^2$ hour of theophylline from suspension in PG.

TABLE 3

PHYSICOCHEMICAL PROPERTIES OF 1-ALKYLOXYCARBONYL DERIVATIVES OF 5-FU

[Chemical structure: pyrimidine ring with R-N, O, F, N-R' substituents]

| Compound | MP °C. | $K^a$ | $C_w{}^b$ |
|---|---|---|---|
| 7. R = H, R' = (C=O)OCH$_3$ | 158–160 | 0.026 | 16.0 |
| 8. R = H, R' = (C=O)OC$_2$H$_5$ | 126.5–128.5 | 0.0757 | 35.2 |
| 9. R = H, R' = (C=O)OC$_3$H$_7$ | 124–126 | 0.359 | 9.2 |
| 10. R = H, R' = (C=O)OC$_4$H$_9$ | 97–98 | 1.46 | 5.36 |
| 11. R = H, R' = (C=O)OC$_6$H$_{13}$ | 66–77 | 31.1 | 1.17 |
| 12. R = H, R' = (C=O)OC$_8$H$_{17}$ | 97–98 | — | — |

[a] Partition coefficient between IPM and pH 4.0 acetate buffer at 23 ± 1° C.
[b] Solubility in mg/ml of pH 4.0 acetate buffer at 23 ± 1° C. calculated from partition coefficient between IPM and pH 4.0 acetate buffer and the solubility of derivative in IPM.

TABLE 4

PHYSICOCHEMICAL PROPERTIES OF 1-ALKYLOXYCARBONYL DERIVATIVES OF 5-FU[a]

| Compound | log $K^b$ | $C_w{}^c$ | Half-Lives (min)[d] Buffer | Half-Lives (min)[d] 80% Plasma |
|---|---|---|---|---|
| 5-FU | −0.83 | 11.1 | | |
| 7 | −0.68 | 23.3 | 190 | — |
| 8 | −0.17 | 6.9 | 550 | 2.1 |
| 9 | — | — | — | — |
| 10 | 0.89 | 5.9 | 550 | 3.1 |
| 11 | 2.04$^e$ | 1.5$^e$ | 550$^e$ | 2.0$^e$ |
| 12 | — | — | — | — |

[a] From J. Pharm. Sci., Vol. 75, page 522, Buur et al (1986).
[b] Octanol-pH 4.0 acetate buffer partition coefficient determined at 22° C.
[c] Solubility in mg/ml at pH 4.0 acetate buffer at 22° C.
[d] Half-lives determined at 37° C. in 0.05 M phosphate buffer at pH 7.4. Plasma was human plasma.
[e] From Int. J. Pharm., Vol. 36, page 41, Buur et al (1987).

TABLE 5

RATES OF DELIVERY OF 5-FU THROUGH HAIRLESS MOUSE SKIN BY 1-ALKYLOXYCARBONYL DERIVATIVES OF 5-FU

| Compound | $C_{IPM}{}^a$ | $J_i{}^b$ | $C_s{}^c$ | $J_j{}^d$ |
|---|---|---|---|---|
| 7 | 0.400 (0.277) | 0.343 | 1.08 | 0.337 |
| 8 | 2.64 (1.70) | 0.770 | 2.38 | 0.357 |
| 9 | 3.28 (1.98) | 0.294 | 0.65 | 0.300 |
| 10 | 7.77 (4.39) | 0.284 | 0.54 | 0.321 |
| 11 | 8.7 (14.4) | 0.195 | 1.38 | 0.321 |
| 12 | 10.4 (4.72) | 0.037 | 0.41 | 0.323 |

[a] Solubility in mg/ml of IPM at 23 ± 1° C. (equivalent mg of 5-FU/ml).
[b] Flux in mg/cm$^2$ hour of 5-FU from suspensions of prodrugs in IPM.
[c] Amount of 5-FU in mg leached from hairless mouse skin in 24 hours subsequent to application of prodrug in vehicle for 48 hours.
[d] Flux in mg/cm$^2$ hour of theophylline from suspension in PG.

TABLE 6

PHYSICOCHEMICAL PROPERTIES OF 3-ALKYLCARBONYL DERIVATIVES OF 5-FU

[Chemical structure: pyrimidine ring with R-N, O, F, N-R' substituents]

| Compound | MP °C. | $K^b$ | $C_w{}^c$ |
|---|---|---|---|
| 13. R = (C=O)CH$_3$, R' = H | 114–117[a] | 0.040 | 18.5 |
| 14. R = (C=O)C$_2$H$_5$, R' = H | 99–102[a] | 0.088 | 29.9 |
| 15. R = (C=O)C$_3$H$_7$, R' = H | 111–112 | 0.97 | 4.59 |
| 16. R = (C=O)C$_4$H$_9$, R' = H | 110–111 | 1.65 | 1.19 |

[a] From J. Med. Chem., Vol. 23, page 1324, Kametani et al (1980).
[b] Partition coefficient between IPM and pH 4.0 acetate buffer at 23 ± 1° C.
[c] Solubility in mg/ml of pH 4.0 acetate buffer at 23 ± 1° C. calculated from partition coefficient between IPM and pH 4.0 acetate buffer and the solubility of derivative in IPM.

TABLE 7

PHYSICOCHEMICAL PROPERTIES OF 3-ALKYLOXYCARBONYL DERIVATIVES OF 5-FU[a]

| Compound | log $K^b$ | $C_w{}^c$ | Half-Lives (min)[d] Buffer | Half-Lives (min)[d] 80% Plasma |
|---|---|---|---|---|
| 13 | −0.34 | 42.8 | 43 | 4.6 |
| 14 | 0.19 | 35.3 | 50 | 20 |
| 15 | 0.67 | — | 58 | 28 |

[a] From Int. J. Pharm., Vol. 21, page 349, Buur et al (1984).
[b] Octanol-pH 4.0 acetate buffer partition coefficient determined at 22° C.
[c] Solubility in mg/ml at pH 4.0 acetate buffer at 22° C.
[d] Half-lives determined at 37° C. in 0.05 M phosphate buffer at pH 7.4. Plasma was human plasma.

TABLE 8

RATES OF DELIVERY OF 5-FU THROUGH HAIRLESS MOUSE SKIN BY 3-ALKYLCARBONYL DERIVATIVES OF 5-FU

| Compound | $C_{IPM}{}^a$ | $J_i{}^b$ | $C_s{}^c$ | $J_j{}^d$ |
|---|---|---|---|---|
| 13 | 0.074 (0.56) | 0.575 | 1.77 | 0.282 |
| 14 | 2.62 (1.83) | 0.673 | 2.00 | 0.318 |
| 15 | 4.44 (2.89) | 0.291 | 0.86 | 0.204 |
| 16 | 1.96 (1.19) | 0.071 | 0.38 | 0.194 |

[a] Solubility in mg/ml of IPM at 23 ± 1° C. (equivalent mg of 5-FU/ml).
[b] Flux in mg/cm$^2$ hour of 5-FU from suspensions of prodrugs in IPM.
[c] Amount of 5-FU in mg leached from hairless mouse skin in 24 hours subsequent to application of prodrug in vehicle for 48 hours.
[d] Flux in mg/cm$^2$ hour of theophylline from suspension in PG.

TABLE 9

PHYSICOCHEMICAL PROPERTIES OF
1,3-BISALKYLCARBONYL DERIVATIVES OF 5-FU

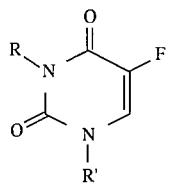

| Compound | MP °C. | $K^a$ | $C_w^b$ |
|---|---|---|---|
| 17. R = R' = (C=O)CH$_3$ | 109–111 | 2.93 | 1.91 |
| 18. R = R' = (C=O)C$_2$H$_5$ | 97–99 | 33.8 | 0.80 |
| 19. R = R' = (C=O)C$_3$H$_7$ | 46–48 | — | — |
| 20. R = R' = (C=O)C$_4$H$_9$ | 44–46 | — | — |

$^a$Partition coefficient between IPM and pH 4. 0 acetate buffer at 23 ± 1° C.
$^b$Solubility in mg/ml of pH 4.0 acetate buffer at 23 ± 1° C. calculated from partition coefficient between IPM and pH 4.0 acetate buffer and the solubility of derivative in IPM.

TABLE 10

RATES OF DELIVERY OF 5-FU THROUGH
HAIRLESS MOUSE SKIN BY
1,3-BISALKYLCARBONYL DERIVATIVES OF 5-FU

| Compound | $C_{IPM}^a$ | $J_i^b$ | $C_s^c$ | $J_j^d$ |
|---|---|---|---|---|
| 17 | 5.60 (3.40) | 0.291 | 1.24 | 0.282 |
| 18 | 17.4 (9.35) | 0.090 | 0.51 | 0.288 |
| 19 | 169 (81.4) | 0.127 | 1.54 | 0.190 |
| 20 | 352 (154) | 0.124 | 1.14 | 0.156 |

$^a$Solubility in mg/ml of IPM at 23 ± 1° C. (equivalent mg of 5-FU/ml).
$^b$Flux in mg/cm$^2$ hour of 5-FU from suspensions of prodrugs in IPM.
$^c$Amount of 5-FU in mg leached from hairless mouse skin in 24 hours subsequent to application of prodrug in vehicle for 48 hours.
$^d$Flux in mg/cm$^2$ hour of theophylline from suspension in PG.

While we have described various embodiments in accordance with the present invention, it is understood that the same is not limited thereto, but is susceptible of numerous changes and modifications as known to those skilled in the art. Therefore, we do not wish to be limited to the details described herein, but intend to cover all such changes and modifications as are encompassed by the scope of the appended claims.

We claim:

1. A pharmaceutical composition in unit dosage form adapted for topical administration to the skin of a human or non-human animal in need of the pharmacological activity of 5-fluorouracil comprising a pharmacologically effective amount of a prodrug of 5-fluorouracil having the formula:

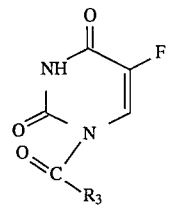

wherein R$_3$ is bonded to said C=O by a carbon to carbon bond and is a group such that said prodrug (1) has an enhanced delivery across topical membranes of said animal upon topical application of said composition as compared with 5-fluorouracil and (2) hydrolyzes after delivery across said topical membrane to yield a pharmacologically effective amount of 5-fluorouracil.

2. A composition according to claim 1, wherein R$_3$ is selected from the group consisting of (a) cycloalkyl groups having four to ten carbon atoms, (b) straight or branched chain alkyl groups of one to ten carbon atoms, (c) straight or branched chain alkenyl or alkynyl groups of two to ten carbon atoms, wherein the chains of (a), (b) or (c) thereof (1) may be interrupted by one or more N, S or O atoms, or (2) may be substituted at any point on the chain by one or more members selected from the group consisting of COR$_5$, COOR$_5$, CON(R$_5$)$_2$ and mono- and bi-cyclic saturated or unsaturated heterocyclic rings, each ring consisting of three to seven members selected from the group consisting of C, N, O and S, hydrocarbyl aryl groups, aryl groups substituted by at least one member selected from the group consisting of COR$_5$, COOR$_5$, CON(R$_5$)$_2$, OR$_5$, halogen, SR$_5$, N(R$_5$)$_2$, NO$_2$ and R$_5$, and mono- and bi-cyclic saturated or unsaturated heterocyclic rings, each ring consisting of three to seven members selected from the group consisting of C, N, O and S; and R$_5$ is selected from the group consisting of cycloalkyl groups of four to ten carbon atoms, straight or branched chain alkyl groups of one to ten carbon atoms, and alkenyl or alkynyl groups of two to ten carbon atoms.

3. A composition according to claim 2, wherein R$_3$ is CH$_3$ or C$_2$H$_5$.

4. A composition according to claim 2, wherein R$_3$ is C$_2$H$_5$.

5. A composition according to claim 1, wherein said prodrug of 5-fluorouracil has the formula:

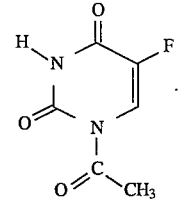

6. A method of administering 5-fluorouracil to a human or non-human animal in need of the pharmacological activity of 5-fluorouracil comprising topically applying to said animal a pharmacologically effective amount of a composition according to claim 1.

7. A method according to claim 6, wherein R$_3$ is selected from the group consisting of (a) cycloalkyl groups having four to ten carbon atoms, (b) straight or branched chain alkyl groups of one to ten carbon atoms, (c) straight or branched chain alkenyl or alkynyl groups of two to ten carbon atoms, wherein the chains of (a), (b) or (c) thereof (1) may be interrupted by one or more N, S or O atoms, or (2) may be substituted at any point on the chain by one or more members selected from the group consisting of COR$_5$, COOR$_5$, CON(R$_5$)$_2$ and mono- and bi-cyclic saturated or unsaturated heterocyclic rings, each ring consisting of three to seven members selected from the group consisting of C, N, O and S, hydrocarbyl aryl groups, aryl groups substituted by at least one member selected from the group consisting of COR$_5$, COOR$_5$, CON(R$_5$)$_2$, OR$_5$, halogen, SR$_5$, N(R$_5$)$_2$, NO$_2$ and R$_5$, and mono- and bi-cyclic saturated or unsaturated heterocyclic rings, each ring consisting of three to seven members selected from the group consisting of C, N, O and S; and R$_5$ is selected from the group consisting of cycloalkyl groups of four to ten carbon atoms, straight or branched chain alkyl groups of one to ten carbon atoms, and alkenyl or alkynyl groups of two to ten carbon atoms.

8. A method according to claim 7, wherein R$_3$ is CH$_3$ or C$_2$H$_5$.

9. A method according to claim 7, wherein R$_3$ is C$_2$H$_5$.

10. A method according to claim 6, wherein said prodrug of 5-fluorouracil has the formula:

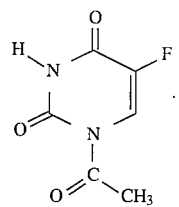

* * * * *